United States Patent
Krüger et al.

(10) Patent No.: US 6,673,747 B2
(45) Date of Patent: Jan. 6, 2004

(54) HERBICIDAL COMPOSITION COMPRISING PRETILACHLOR OR PYRIFTALID WITH SULFONYLUREAS

(75) Inventors: Christian Krüger, Grenzach-Wyhlen (DE); Jean-Louis Allard, Rheinfelden (CH); Christoph Labhart, Himmelried (CH)

(73) Assignee: Syngenta Participations AG (CH)

( * ) Notice: Subject to any disclaimer, the term of this patent is extended or adjusted under 35 U.S.C. 154(b) by 0 days.

(21) Appl. No.: 10/173,271

(22) Filed: Jun. 17, 2002

(65) Prior Publication Data

US 2002/0193253 A1 Dec. 19, 2002

Related U.S. Application Data

(63) Continuation of application No. 09/849,817, filed on May 4, 2001, now abandoned.

(30) Foreign Application Priority Data

Nov. 4, 1998 (CH) .............................................. 2222/98

(51) Int. Cl.⁷ ..................... A01N 37/22; A01N 43/54; A01N 47/36

(52) U.S. Cl. .................. 504/133; 504/134; 504/135; 504/136; 504/211; 504/243; 504/342

(58) Field of Search .................. 504/133, 134, 504/135, 136, 243, 342, 211

(56) References Cited

U.S. PATENT DOCUMENTS

| | | | | |
|---|---|---|---|---|
| 4,840,663 A | | 6/1989 | Quadranti et al. | 504/133 |
| 5,217,525 A | | 6/1993 | Quadranti et al. | 504/135 |
| 5,849,665 A | * | 12/1998 | Gut et al. | 504/134 |
| 5,869,428 A | * | 2/1999 | Morishima et al. | 504/215 |
| 6,066,596 A | | 5/2000 | Allard et al. | 504/136 |

FOREIGN PATENT DOCUMENTS

| | | |
|---|---|---|
| EP | 0 456 198 | 11/1991 |
| EP | 0 768 034 | 4/1997 |
| FR | 2 605 497 | 4/1988 |

* cited by examiner

Primary Examiner—S. Mark Clardy
(74) Attorney, Agent, or Firm—Thomas Hamilton

(57) ABSTRACT

Liquid herbicidal composition, containing a grass herbicide that is suspended or dissolved in a non-aqueous liquid phase, a herbicide of the sulfonylurea type that is suspended in a non-aqueous liquid phase, and at least one surface-active substance.

10 Claims, No Drawings

HERBICIDAL COMPOSITION COMPRISING PRETILACHLOR OR PYRIFTALID WITH SULFONYLUREAS

This application is a continuation of Ser. No. 09/849,817, filed May 4, 2001 abandoned.

The present invention relates to a new liquid herbicidal composition, the preparation thereof, as well as the use of the composition in the control of undesired plant growth in crops of cultivated plants.

According to the present invention, a liquid herbicidal composition is proposed, which contains, in addition to customary formulation excipients, (a) at least one grass herbicide that is suspended or dissolved in a non-aqueous liquid phase, (b) at least one herbicide of the sulfonylurea type that is suspended in a non-aqueous liquid phase, and (c) at least one non-ionic or anionic, surface-active substance or a mixture of the non-ionic and anionic substances.

Grass herbicides which may be used in accordance with the invention belong especially to the chemical classes of acetanilides, phenoxypropionic acids, pyrimidinyloxybenzoic acids, phenylsulfonyltriazoles, oxyacetamides, oxazolidindiones, phenylbenzamides, pyrimidinyl thiophthalides and indanes, and are preferably pretilachlor, cyhalofop, pyriminobac, cafenstrole, mefenacet, fentrazamid, oxaziclomefon, pentoxazone, etobenzanid, indanofan as well as epoprodan and the compound of formula I

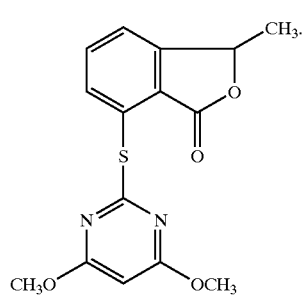

These grass herbicides may also be used in a mixture together. They exist in dissolved or dispersed form in a non-aqueous liquid phase. The herbicides of the sulfonylurea type are also dispersed in preferably the same non-aqueous liquid phase. These are preferably cinosulfuron, pyrazosulfuron, bensulfuron, azimsulfuron, imazosulfuron, ethoxysulfuron, cyclosulfamuron or halosulfuron or mixtures thereof.

The preferred non-aqueous liquid phases include all vegetable and mineral oils, such as rapeseed oil, soybean oil, sunflower oil, castor oil, pine oil, cottonseed oil, as well as derivatives of these oils, for example esters, especially methylesters of these oils, as well as paraffinic and aromatic mineral oils, such as Orchex 796, Shellsol types, Isopar types, aromatic fractions, such as Solvesso 200 and esters such as Exxate 700, as well as mixtures thereof.

The non-ionic and anionic surface-active substances may be conventional, commercially available substances, for example ethoxylated vegetable oils such as Emulsogen EL, ethoxylated fat alcohols such as Genapol O-050, ethoxylated alkylphenols such as Synperonic NP8, ethoxylated polyethylene glycols or polypropylene glycols, e.g. Pluronic types, ethoxylated tristyrylphenol derivatives such as Soprophor 4D384 or Soprophor S/25, oleyl polyglycol ethers such as Genapol U-050, and silicone surfactants such as Silwet L77, as well as dodecylbenzene sulfonates such as Sermul 88A, alcohol ether sulfonates such as Genapol LRO, lignin sulfonates such as Ultrazin NA, phenol sulfonates such as Sipragil GN and polycarboxylates such as Geropon TA72, sulfonated naphthalene/formaldehyde condensates such as Supragil MSN, sulfosuccinates such as Aerosol OT 70 PG, polyacrylate derivatives such as Atlox 4913, maleic acid/olefin copolymers such as Sokolan CP9, alkyl polyglycosides, alkyl succinic acid anhydride derivatives, sorbitan esters, ethoxylated sorbitan esters, alkyl and alkylaryl polyglycol ether phosphoric acid esters and ethoxylated fatty acid esters, as well as taurides such as Hostapon T hk.

The above-mentioned herbicides are described in the Pesticide Manual, Eleventh Edition, British Crop Protection Council, 1997. The compound of formula I is known from EP-A-447506, fentrazamid from British Crop Protection Conference Proceedings, 1997, 67–72, and oxaziclomefon from British Crop Protection Conference Proceedings, 1997, 73–80.

Preferred herbicidal compositions according to the present invention contain as the grass herbicide cyhalofop, pyriminobac, cafenstrole, mefenacet, fentrazamid, oxaziclomefon, pentoxazone, etobenzanid, indanofan, epoprodan, pretilachlor or a compound of formula I

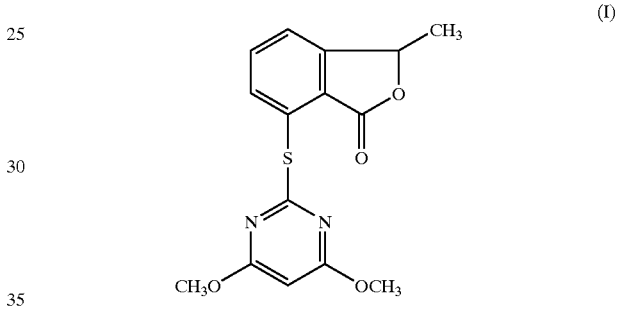

or mixtures thereof.

As the herbicide of the sulfonylurea type, the compositions according to the invention preferably contain pyrazosulfuron, bensulfuron, azimsulfuron, imazosulfuron, ethoxysulfuron, cyclosulfamuron, halosulfuron or cinosulfuron or mixtures thereof.

The non-aqueous liquid phases to be used are preferably mineral oils or vegetable oils, or also mixtures thereof. The preferred non-ionic, surface-active substances that may be considered are ethoxylated vegetable oil, ethoxylated fat alcohol, ethoxylated alkylphenol, ethoxylated polyethylene glycol and polypropylene glycol and copolymers thereof, ethoxylated tristyrylphenol derivative, oleyl polyglycol ether or silicone surfactant, and the anionic surface-active substance may be a dodecylbenzene sulfonate, sulfosuccinate, ethoxylated tristyrylphenol sulfate or phosphate, alcohol ether sulfonate, lignin sulfonate, ethoxylated phenol sulfonate or polycarboxylate.

A significant composition is one which contains as the grass herbicide pretilachlor or the compound of formula I or a mixture thereof suspended or dissolved in a vegetable oil, as the herbicide of the sulfonylurea type bensulfuron, pyrazosulfuron, azimsulfuron, imazosulfuron or cinosulfuron or mixtures thereof suspended in a vegetable oil, and as the surface-active substance a mixture of non-ionic and anionic compounds. Of these, preference is given to a composition which contains as the grass herbicide the compound of formula I suspended or dissolved in a vegetable oil, as the herbicide of the sulfonylurea type cinosulfuron suspended in a vegetable oil, and as the surface-active substance a mixture of non-ionic and anionic compounds. Of these, further preference is given to a composition which contains as the grass herbicide pretilachlor suspended or dissolved in a vegetable oil, as the herbicide of the sulfonylurea type cinosulfuron suspended in a vegetable oil, and as the surface-active substance a mixture of non-ionic and anionic compounds.

An especially effective composition contains as the grass herbicide pretilachlor or the compound of formula I or a mixture thereof, preferably the compound of formula I alone, suspended or dissolved in rapeseed oil or rapeseed oil methyl ester or in a mixture thereof, as the herbicide of the sulfonylurea type bensulfuron suspended in rapeseed oil or rapeseed oil methyl ester or in a mixture thereof, and as the surface-active substance a mixture of a non-ionic with an anionic compound selected from castor oil ethoxylate, dodecylbenzene sulfonate, ethoxylated tristyrylphenol sulfate and oleyl polyglycol ether.

The compositions according to the invention have the great advantage that they may contain the herbicidal active ingredients in high concentrations, and that they remain protected from decomposition over a longer period of time. They also offer the possibility that other oil-soluble or liquid admixtures may be added without problems, such as additives that are suitable for increasing the biological activity, as well as stabilisers such as epoxidised vegetable oils. Surprisingly, the compositions according to the invention show practically no damage to the crops of cultivated plants after their application, despite using organic liquids.

The compositions according to the invention are preferably suitable for the control of weeds in flooded paddy fields. The process is advantageously carried out in such a way that the required amount of composition is mixed with the same amount or up to ten times the amount of water, and applied directly to the already flooded paddy field, or is added to the water flowing in during flooding of the paddy field (so-called splash application). Furthermore, it is also possible, to apply the composition dropwise or in portions simultaneously with the mechanical planting of the rice plants (so-called dip application). Spray application of the composition according to the invention is similarly possible, but requires a higher dilution with water.

The application rates of composition according to the invention may vary within a wide range. It is preferable to use 50 to 2000 g/ha herbicide (grass herbicide plus herbicide of the sulfonylurea type).

The liquid compositions according to the invention contain per liter preferably 30 to 1920 g grass herbicide and 20 to 80 g herbicide of the sulfonylurea type, as well as 50 to 300 g of surface-active substance (anionic plus non-ionic). Normally, 2–20 l/ha of the formulations described below by way of example are required for direct application or for splash application. For spray application, this amount is usually 20–500 l/ha. The compositions according to the invention may also contain further customary additives, for example inert carriers such as kaolin and chalk, stabilisers, anti-foaming agents, preservatives, viscosity regulators, thickeners such as silicic acid or bentonite, binders, tackifiers, as well as fertilisers or other active ingredients. The compositions are produced in known manner, e.g. by intimately mixing and/or grinding the active ingredients with the formulation excipients and with liquid or solid carriers. Particularly preferred formulations are made up as follows:

FORMULATION EXAMPLES

| Substance | Trade name | function | conc. g/l |
|---|---|---|---|
| F1: | | | |
| Compound of formula I | | active ingredient | 180 |
| pretilachlor | Rifit, Solnet | active ingredient | 180 |
| bensulfuron methyl | Londax | active ingredient | 51 |
| castor oil ethoxylate 18EO | Alkamuls R/81 | surface-active substance | 80 |
| dodecylbenzene sulfonate | Sermul EA88 | surface-active substance | 50 |
| rapeseed oil methyl ester | Edenor ME-SU | non-aqueous liquid phase | 20 |
| rapeseed oil | | non-aqueous liquid phase | remainder to make up 1 l |
| F2: | | | |
| Compound of formula I | | active ingredient | 180 |
| pretilachlor | Rifit, Solnet | active ingredient | 180 |
| bensulfuron methyl | Londax | active ingredient | 51 |
| ethoxylated tristyryiphenol sulfate | Soprophor 4D384 | surface-active substance | 20 |
| dodecylbenzene sulfonate | Sermul EA88 | surface-active substance | 40 |
| oleyl polyglycol ether | Genapol U-050 | surface-active substance | 90 |
| mineral oil | Orchex 796 | non-aqueous liquid phase | remainder to make up 1 l |

-continued

| Substance | Trade name | function | conc. g/l |
|---|---|---|---|
| F3: | | | |
| Compound of formula I | | active ingredient | 180 |
| pretilachlor | Rifit, Solnet | active ingredient | 180 |
| bensulfuron methyl | Londax | active ingredient | 51 |
| ethoxylated tristyrylphenol sulfate | Soprophor 4D384 | surface-active substance | 20 |
| dodecylbenzene sulfonate | Sermul EA88 | surface-active substance | 50 |
| castor oil ethoxylate 18EO | Alkamuls R/81 | surface-active substance | 80 |
| rapeseed oil methyl ester | Edenor ME-SU | non-aqueous liquid phase | remainder to make up 1 l |
| F4: | | | |
| Compound of formula I | | active ingredient | 180 |
| pretilachlor | Rifit, Solnet | active ingredient | 180 |
| bensulfuron methyl | Londax | active ingredient | 51 |
| castor oil derivative | Marlowet LVS | surface-active substance | 150 |
| rapeseed oil | | non-aqueous liquid phase | remainder to make up 1 l |
| F5: | | | |
| Compound of formula I | | active ingredient | 180 |
| pretilachlor | Rifit, Solnet | active ingredient | 180 |
| bensulfuron methyl | Londax | active ingredient | 30 |
| azimsulfuron | Gulliver | active ingredient | 6 |
| dodecylbenzene sulfonate | Sermul EA88 | surface-active substance | 50 |
| castor oil ethoxylate | Sermul EN24 | surface-active substance | 50 |
| silicic acid | Aerosil 200 | thickener | 20 |
| rapeseed oil | | non-aqueous liquid phase | 234 |
| rapeseed oil methyl ester | Agrimul 2232 F | non-aqueous liquid phase | remainder to make up 1 l |
| F6: | | | |
| Compound of formula I | | active ingredient | 180 |
| pretilachlor | Rifit, Solnet | active ingredient | 180 |
| bensulfuron methyl | Londax | active ingredient | 30 |
| azimsulfuron | Gulliver | active ingredient | 6 |
| dodecylbenzene sulfonate | Sermul EA88 | surface-active substance | 65 |
| castor oil ethoxylate | Sermul EN24 | surface-active substance | 65 |
| tristyrylphenol ethoxylate | Soprophor BSU | surface-active substance | 20 |
| silicic acid | Aerosil 200 | thickener | 30 |
| rapeseed oil | | non-aqueous liquid phase | 174 |
| rapeseed oil methyl ester | Agrimul 2232 F | non-aqueous liquid phase | remainder to make up 1 l |
| F7: | | | |
| Compound of formula I | | active ingredient | 180 |
| cinosulfuron | Setoff | active ingredient | 24 |
| ethoxylated tristyrylphenol sulfate | Soprophor 4D384 | surface-active substance | 20 |
| castor oil ethoxylate | Sermul EN24 | surface-active substance | 40 |

-continued

| Substance | Trade name | function | conc. g/l |
|---|---|---|---|
| dodecylbenzene sulfonate | Sermul EA88 | surface-active substance | 40 |
| silicic acid | Aerosil 200 | thickener | 40 |
| rapeseed oil methyl ester | Agrimul 2232 F | non-aqueous liquid phase | remainder to make up 1 l |

F8:

| Substance | Trade name | function | conc. g/l |
|---|---|---|---|
| Compound of formula I | | active ingredient | 180 |
| cinosulfuron | Setoff | active ingredient | 24 |
| ethoxylated tristyrylphenol sulfate | Soprophor 4D384 | surface-active substance | 20 |
| castor oil ethoxylate | Sermul EN24 | surface-active substance | 65 |
| dodecylbenzene sulfonate | Sermul EA88 | surface-active substance | 65 |
| silicic acid | Aerosil 200 | thickener | 40 |
| aluminium silicate | Attagel 50 | inert carrier | 30 |
| rapeseed oil methyl ester | Agrimul 2232 F | non-aqueous liquid phase | remainder to make up 1 l |

F9:

| Substance | Trade name | function | conc. g/l |
|---|---|---|---|
| pretilachlor | Rifit | active ingredient | 450 |
| cinosulfuron | Setoff | active ingredient | 24 |
| ethoxylated tristyrylphenol sulfate | Soprophor 4D384 | surface-active substance | 20 |
| castor oil ethoxylate | Sermul EN24 | surface-active substance | 60 |
| dodecylbenzene sulfonate | Sermul EA88 | surface-active substance | 60 |
| aluminium silicate | Kaolin | inert carrier | 250 |
| silicic acid | Aerosil 200 | thickener | 30 |
| rapeseed oil methyl ester | Agrimul 2232 F | non-aqueous liquid phase | remainder to make up 1 l |

F10:

| Substance | Trade name | function | conc. g/l |
|---|---|---|---|
| pretilachlor | Rifit | active ingredient | 450 |
| cinosulfuron | Setoff | active ingredient | 24 |
| ethoxylated tristyrylphenol sulfate | Soprophor 4D384 | surface-active substance | 20 |
| castor oil ethoxylate | Sermul EN24 | surface-active substance | 60 |
| dodecylbenzene sulfonate | Sermul EA88 | surface-active substance | 60 |
| aluminium silicate | Kaolin | inert carrier | 200 |
| silicic acid | Aerosil 200 | thickener | 30 |
| rapeseed oil methyl ester | Agrimul 2232 F | non-aqueous liquid phase | remainder to make up 1 l |

APPLICATION EXAMPLES

Formulations F1, F2, F3, F4, F5, F6, F7, F8, F9 and F10 are diluted with water to 5 liters, and introduced directly to a flooded paddy field at an application rate of 5 l/ha (splash application). 22 days after application, control of the weeds Echinochloa, Scirpus and Monochoria is investigated, as well as the phytotoxic activity of the compositions on rice (100% indicates complete control of the weeds or completely withered rice, 0% indicates no control of the weeds or no phytotoxic activity on the rice). This takes place in tests running in parallel: a) upon emergence, b) at the 2.5 leaf stage and c) at the 4.1 leaf stage of Echinochloa. The results obtained in these tests are summarised in the following Table:

| Formulation | | % weed control % phytotoxic activity | | |
|---|---|---|---|---|
| | | a) | b) | c) |
| F1 | rice | 0 | 5 | 11 |
| | Echinochloa | 99 | 96 | 95 |
| | Scirpus | 98 | 92 | 94 |
| | Monochoria | 100 | 95 | 95 |
| F2 | rice | 0 | 7 | 9 |
| | Echinochloa | 99 | 98 | 92 |

-continued

| Formulation | | % weed control % phytotoxic activity | | |
| --- | --- | --- | --- | --- |
| | | a) | b) | c) |
| | Scirpus | 98 | 94 | 94 |
| | Monochoria | 100 | 94 | 93 |
| F3 | rice | 3 | 8 | 9 |
| | Echinochloa | 100 | 95 | 93 |
| | Scirpus | 99 | 90 | 95 |
| | Monochoria | 100 | 89 | 96 |
| F5 | rice | 0 | 0 | |
| | Echinochloa | 100 | 70 | |
| | Scirpus | 90 | 80 | |
| | Monochoria | 95 | 90 | |
| F6 | rice | 0 | 0 | |
| | Echinochloa | 100 | 80 | |
| | Scirpus | 90 | 80 | |
| | Monochoria | 98 | 90 | |
| F7 | rice | 0 | 0 | |
| | Echinochloa | 98 | 70 | |
| | Scirpus | 70 | 80 | |
| | Monochoria | 90 | 90 | |
| F8 | rice | 0 | 0 | |
| | Echinochloa | 98 | 70 | |
| | Scirpus | 70 | 90 | |
| | Monochoria | 95 | 90 | |
| F9 | rice | 0 | 0 | |
| | Echinochloa | 100 | 20 | |
| | Scirpus | 98 | 90 | |
| | Monochoria | 100 | 95 | |
| F10 | rice | 0 | 0 | |
| | Echinochloa | 100 | 10 | |
| | Scirpus | 95 | 90 | |
| | Monochoria | 100 | 90 | |

The same results are obtained if these formulations are diluted with water, e.g. to 2–500 l.

What is claimed is:

1. Liquid herbicidal composition, containing
   (a) at least one grass herbicide that is suspended or dissolved in a vegetable or mineral oil or a mixture of these oils, said grass herbicide comprising at least one member selected from the group consisting of the compound of formula (I),

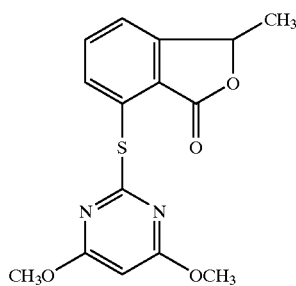

pretilachlor and mixtures thereof,
   (b) at least one herbicide of the sulfonylurea type that is suspended in a vegetable or mineral oil or a mixture of these oils, and
   (c) at least one non-ionic or anionic, surface-active substance or a mixture of the non-ionic and anionic surface-active substances.

2. Composition according to claim 1, containing as the herbicide of the sulfonylurea type pyrazosulfuron, bensulfuron, azimsulfuron, imazosulfuron, ethoxysulfuron, cyclosulfamuron, halosulfuron or cinosulfuron or a mixture thereof.

3. Composition according to claim 1, containing as the vegetable or mineral oil at least one member selected from the group consisting of rapeseed oil, soybean oil, sunflower oil, castor oil, pine oil, cottonseed oil, including derivatives of these oils, paraffinic mineral oils and aromatic mineral oils.

4. Composition according to claim 1, containing as the non-ionic, surface-active substance, an ethoxylated vegetable oil, ethoxylated fat alcohol, ethoxylated alkylphenol, ethoxylated polyethylene glycol or propylene glycol or copolymers thereof, ethoxylated tristyrylphenol derivative, oleyl polyglycol ether or silicone surfactant, or as the anionic surface-active substance, a dodecylbenzene sulfonate, sulfosuccinate, ethoxylated tristyrylphenol sulfate or phosphate, alcohol ether sulfonate, lignin sulfonate, ethoxylated phenol sulfate or polycarboxylate or a mixture of these non-ionic and anionic, surface-active compounds.

5. Composition according to claim 1, containing as the grass herbicide pretilachlor or the compound of formula I or a mixture thereof suspended or dissolved in a vegetable oil, as the herbicide of the sulfonylurea type bensulfuron, pyrazosulfuron, azimsulfuron, imazosulfuron or cinosulfuron or mixtures thereof suspended in a vegetable oil, and as the surface-active substance a mixture of non-ionic and anionic compounds, selected from the group consisting of ethoxylated vegetable oil, ethoxylated fat alcohol, ethoxylated alkylphenol, ethoxylated polyethylene glycol or propylene glycol or copolymers thereof, ethoxylated tristyrylphenol derivative, oleyl polyglycol ether and silicone surfactant, dodecylbenzene sulfonate sulfosuccinate, ethoxylated tristyrylphenol sulfate or phosphate, alcohol ether sulfonate, lignin sulfonate, ethoxylated phenol sulfate and polycarboxylate.

6. Composition according to claim 5, containing as the grass herbicide the compound of formula I and as the herbicide of the sulfonylurea type cinosulfuron.

7. Composition according to claim 5, containing as the grass herbicide pretilachlor and as the herbicide of the sulfonylurea type cinosulfuron.

8. Composition according to claim 5, containing as the grass herbicide pretilachlor or the compound of formula I or a mixture thereof, suspended or dissolved in rapeseed oil or rapeseed oil methyl ester or in a mixture thereof, as the herbicide of the sulfonylurea type bensulfuron suspended in rapeseed oil or rapeseed oil methyl ester or in a mixture thereof, and as the surface-active substance a mixture of a non-ionic with an anionic compound selected from castor oil ethoxylate, dodecylbenzene sulfonate, ethoxylated tristyrylphenol sulfate and oleyl polyglycol ether.

9. Composition according to claim 8, containing as the grass herbicide the compound of formula I.

10. A method for controlling undesired plant growth in rice crops said method comprising direct application of the composition of claim 1 to already flooded paddy fields, to paddy fields that are just being flooded, or during planting of the rice plants.

* * * * *